United States Patent

Ono et al.

[11] Patent Number: 5,316,712
[45] Date of Patent: May 31, 1994

[54] PROCESS FOR PRODUCING SOLID COSMETICS

[75] Inventors: Atsushi Ono, Tokyo; Yasumasa Oki, Tokorozawa; Jugoro Okumura, Tokyo, all of Japan

[73] Assignee: JO Cosmetics Co., Ltd., Tokyo, Japan

[21] Appl. No.: 964,023

[22] Filed: Oct. 20, 1992

[30] Foreign Application Priority Data

Apr. 3, 1992 [JP] Japan .................................. 4-125297

[51] Int. Cl.$^5$ ...................... B29C 45/47; B29C 45/53; B29K 91/00
[52] U.S. Cl. ............................. 264/102; 264/211.11; 264/297.8; 264/328.2; 264/328.16; 264/328.18; 264/330; 264/328.8; 425/803; 425/DIG. 32
[58] Field of Search ............ 264/102, 259, 267, 328.2, 264/328.8, 328.17, 328.18, 328.19, 328.4, 330, 328.16, 211, 211.11, 297.8; 425/DIG. 32, 803

[56] References Cited

U.S. PATENT DOCUMENTS

| | | | |
|---|---|---|---|
| 3,315,344 | 4/1967 | Niclas | 264/267 |
| 3,585,265 | 6/1971 | Motsavage et al. | 264/267 |
| 3,940,467 | 2/1976 | Brachman | 264/328.19 |
| 4,069,574 | 1/1978 | Krevald et al. | 264/267 |
| 4,374,796 | 2/1983 | Ogasawaba et al. | 264/267 |
| 4,565,512 | 1/1986 | Wills et al. | 264/102 |
| 4,591,467 | 5/1986 | Kopernicky | 264/102 |
| 4,792,424 | 12/1988 | Loman | 264/102 |
| 4,822,269 | 4/1989 | Kammama et al. | 264/102 |

*Primary Examiner*—Jeffery Thurlow
*Assistant Examiner*—Mathieu Vargot
*Attorney, Agent, or Firm*—Dilworth & Barrese

[57] ABSTRACT

A process of producing a solid cosmetic includes continuously repeating the steps of feeding a cosmetic base containing a powder and an oil as main ingredients into a heating cylinder from a hopper, causing the cosmetic base to be injected into a mold by forward motion of a screw or plunger, and cooling the thus-injected cosmetic base to solidify in the mold.

4 Claims, 3 Drawing Sheets

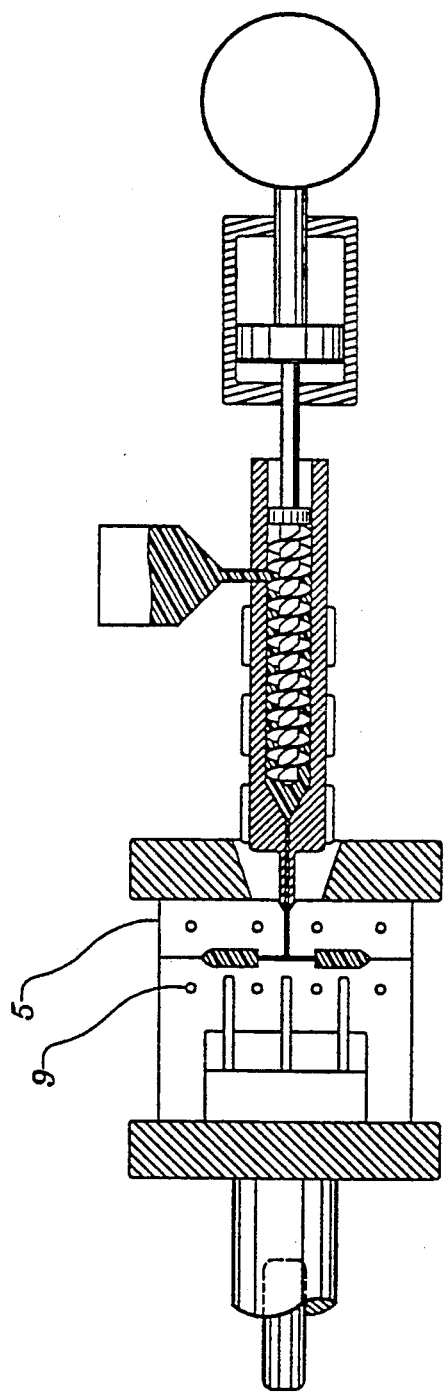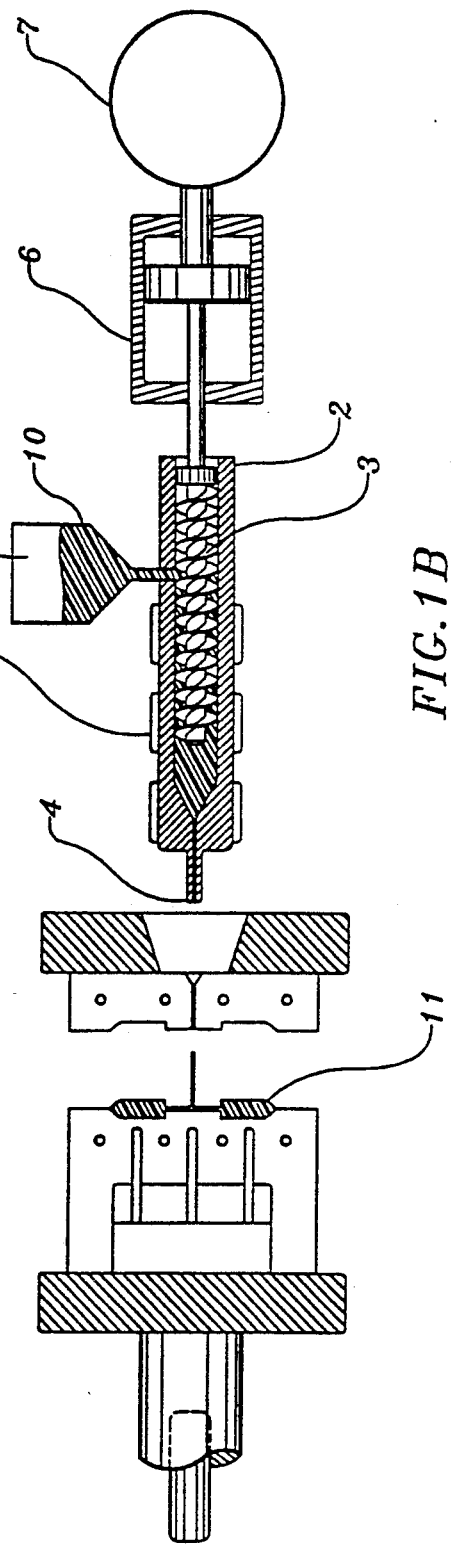
FIG.1A
FIG.1B

PROCESS FOR PRODUCING SOLID COSMETICS

BACKGROUND OF THE INVENTION

The present invention relates to a process for producing a solid cosmetic, involving subjecting a cosmetic base containing appropriate amounts of an oil and a powder as principal ingredients to an injection molding directly in a mold or through ogive mold, capsule, inner plate, container, or the like fitted in the mold. The molded product thus obtained has no unevenness in hardness in the interior thereof and possesses a polymorphous property which permits forming into any desired shape, further possessing a shape retaining property and a sufficient strength. In actual use, the solid cosmetic thus obtained adheres well to the skin and spreads to a satisfactory extent. Moreover, it does not provide a dry or sticky impression, possesses a good cosmetic retaining property, and does not re-adhere to handkerchief, tableware, etc. Further, the molded product exhibits an extrenmely good handleability and the high productivity.

Heretofore, there have been proposed a solvent process wherein a cosmetic base and a volatile solvent are mixed together into a slurry, then the slurry is filled into a container or a mold, thereafter the solvent is removed, followed by solidifying molding (Japanese Patent Laid Open No. 127305/1981) wherein a cosmetic base and a volatile solvent are mixed together into a slurry, then the solvent is absorbed by an absorber while the slurry, which is viscous, is injected at a low pressure, followed by filling and solidifying.

Also, as methods wherein ogive mold, capsule, inner plate, container, or the like, are fitted into a mold and then a cometic base is filled into the thus-loaded member to obtain a molded product, there are known a compression molding wherein an inner plate is fitted into a mold, an injection molding wherein a cosmetic base is injected through an opening formed in the back of a container or an inner plate, a cast molding wherein a cosmetic base is filled by casting into an inner plate or a container to obtain a solid cosmetic, and a method (Japanese Patent Laid Open No. 62513/1984) wherein a cosmetric base is filled by casting into a cylindrical container, then taken out and cut into an appropriate thickness, and the thus-cut piece is filled into a container and pressed at a low pressure to obtain a solid cosmetic. For example, according to the compression molding, an inner plate is loaded to a female mold of a pressing machine and a cosmetic base is filled into the inner plate, thereafter pressure is applied from one side by means of a male mold to obtain a solid cosmetic.

As injection molding methods of injecting a cosmetic base through a small opening formed in the back of a container or an inner plate, there have been proposed a method (Japanese Patent Publication No. 54766/1988) wherein a cosmetic base is dissolved in a solvent and thereby made viscous, then this viscous cosmetic base is injected through a small opening formed in the back of a container or an inner plate and thereafter solidified while the solvent is sucked from the cosmetic base and a method (Japanese Patent Laid Open No. 156709/1988) wherein a viscous cosmetic base is injected through a small opening formed in the back of a container and then solidified by cooling using a cooling plate from the surface opening side of the container.

Solid cosmetics obtained by compression molding are simple in shape and their shapes are limited to planar shapes. When complicated shapes, e.g. spherical and rod-like shapes are to be obtained, compression becomes non-uniform, and during molding and when the cosmetics are applied to the skin, there occurs breakage or cracking. Besides, such cosmetics are unsatisfactory also in the feeling of use such as being low in strength and inferior in both impact strength and adhesion to the skin or to a puff. Also as to the amount of a binder which is used for remedying these drawbacks, there is a limitation. If the amount of the binder is increased, the fluidity of the cosmetic base used is deteriorated, resulting in that the filling thereof into the inner plate from the hopper is no longer smooth, thus causing unevenness in weighing. Thus, in compression molding, there is a restriction not only in the shape of a cosmetic to be obtained but also in point of formulation and it is extremely difficult to produce a solid cosmetic capable of satisfying all of high strength, good feeling of use and desired shape which are important conditions required for cosmetics.

According to a cast dissolving/melting filling method, in the case of filling and molding a cosmetic base into a container or an inner plate, since the filling pressure is low, the cosmetic base to be filled is limited to one which assumes a liquid state of low viscosity when melted. The use of a highly viscous and sticky cosmetic base makes the filling thereof impossible and thus there is a restriction on the formulation of a cosmetic base to be used.

According to a solvent method wherein a cosmetic base which has been dissolved in a solvent is injected and filled and solidified while the solvent is sucked in vacuum, a high strength is obtained when the amount of a binder used is large, but the user feels the cosmetic sticky, and with the lapse of time, the cosmetic will be twisted and cause unevenness. In addition, it becomes necessary to use a special apparatus for recovery of the solvent, thus resulting in increase of the cost. Further, the suction of the solvent causes unevenness in the amount of the binder and that of a coloring matter in the cosmetic, thus making it extremely difficult to effect the filling of the cosmetic in a constant amount. And the injection pressure is as low as 4 to 6 $kg/cm^2$. Thus, this method is unsuitable for the filling of a highly viscous, clay-like cosmetic base and requires a large amount of a solvent for lowering the viscosity. Besides, the resulting molded product is poor in strength.

According to the method wherein a cosmetic base is filled under pressure through a small hole formed in the back of a container and just thereafter cooling is performed using a cooling plate from the surface opening side of the container, since the cooling just after the filling is only at the surface opening portion of the container, the cooling efficiency is low and it takes time until solidifying by the cooling. Thus, not only the productivity is low but also molded products obtained by this method are limited to thin products. Further, since the cosmetic composition used should have fluidity at the time of melting, if the amount of a binder used is large, a restriction is imposed on the formulation, the cosmetic is sticky in use and will be twisted with the lapse of time, causing unevenness.

According to a method wherein a cosmetic composition is cast into a tubular container, then taken out from the tube and cut in round slices, which slices are each filled into a container, followed by pressing at a low pressure, there are the same drawbacks as in the foregoing cast molding method; besides, the process up to completion of the molding is complicated, leading to an increase of the manufacturing cost.

It is the object of the present invention to provide a process for producing a solid cosmetic which has remedied the above-mentioned drawbacks of the prior art.

SUMMARY OF THE INVENTION

Having made extensive studies for achieving the abovementioned object, the present inventors found out that a solid cosmetic free of unevenness in hardness, possessing a polymorphous property which permits forming into any desired shape, also possessing a shape retaining property and a sufficient strength, superior in the adhesion to the skin and spreading proerty, not exhibiting a dry or sticky feeling, further superior in the cosmetic retaining property, and not re-adhering to handkerchief, coffee cup, etc., could be produced in high productivity by automatic molding involving injection-molding into a clamped, plural-cavity mold a cosmetic composition, e.g. a cosmetic composition containing a solid oil-containing oil and a powder as main ingredients, or a cosmetic composition containing a liquid oil and a powder as main ingredients, or a viscous cosmetic composition comprising a cosmetic composition containing an oil and a powder and a solvent (e.g. silicone oil, lower alcohol, isoparaffin, or water) added to the cosmetic composition. In this way we accomplished the present invention.

More specifically, the present invention resides in a process for producing a solid cosmetic, which process comprises feeding a cosmetic base containing a powder and an oil as main ingredients into a heating cylinder incorporating a screw or a plunger therein from a hopper, allowing it to be plasticized, injecting the plasticized mass into a clamped, single- or plural-cavity mold by a forward movement of the screw or the plunger, followed by cooling to solidify, and repeating these steps continously.

BRIEF DESCRIPTION OF THE DRAWINGS

FIG. 1 is a sectional view showing an example of a molding equipment used in the process of the present invention, in which A shows an integral state and B shows a separated state of an injection unit and a mold unit (fixed side and movable side);

Figure 2:
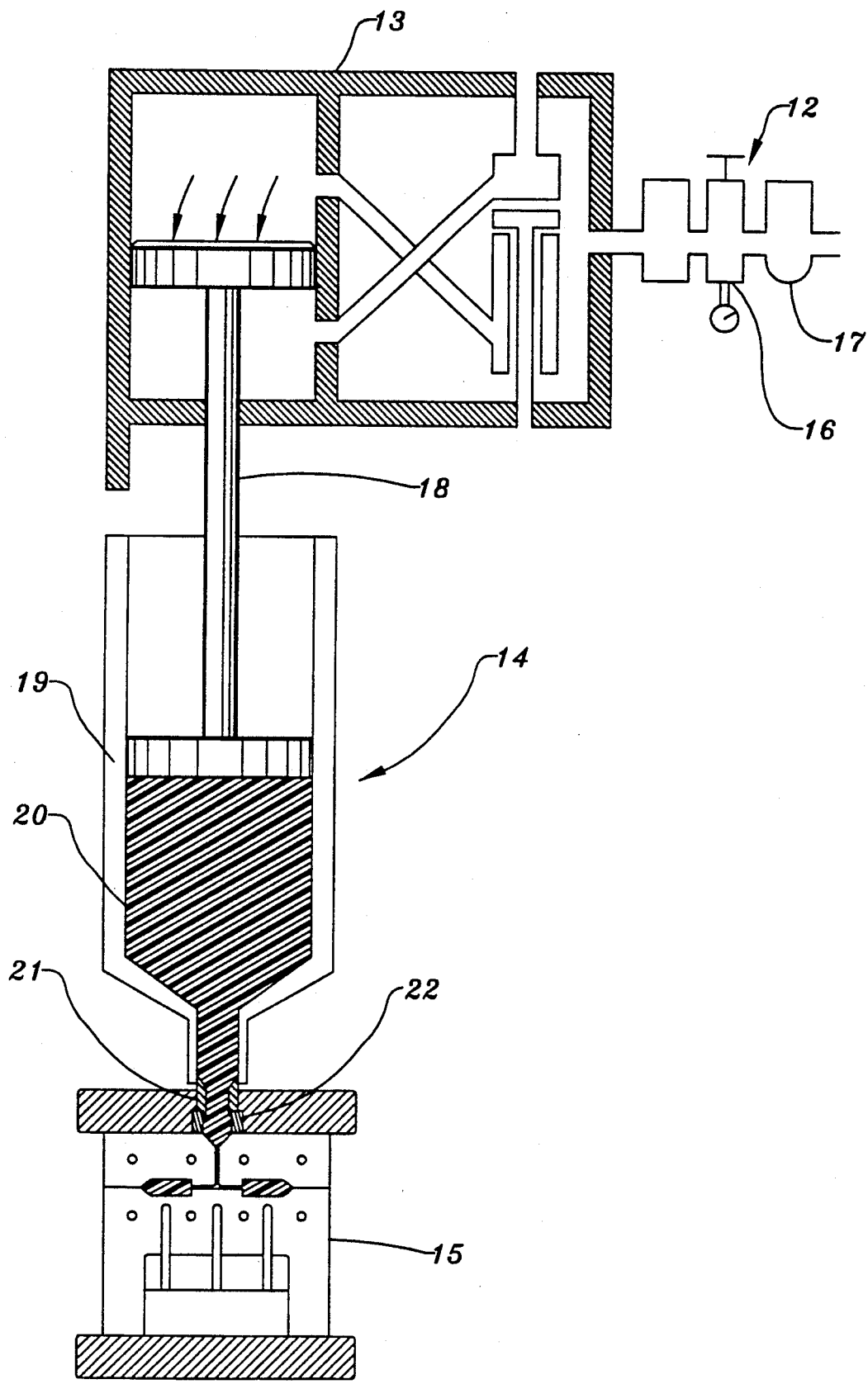
FIG. 2 is a sectional view showing another example of a molding equipment employable in the process of the present invention.

Reference Numerals in FIG. 1:
1 ... hopper
2 ... cylinder
3 ... screw
4 ... nozzle
5 ... mold
6 ... oil-hydraulic cylinder
7 ... oil-hydraulic motor
8 ... heater
9 ... cooling water hole
10 ... material
11 ... molded product
Reference Numerals in FIG. 2:
12 ... air feeder
13 ... air cylinder
14 ... heating cylinder
15 ... mold
16 ... air regulator
17 ... filter
18 ... pump shaft
19 ... jacket (hot water)
20 ... bulk
21 ... nozzle
22 ... shut-off valve
Reference Numerals in FIGS. 3 to 6:
23 ... stationary-side mounting plate
24 ... stationary-side platen
25 ... cavity
26 ... movable-side platen
27 ... spacer block
28 ... ejector plate
29 ... movable-side mounting plate
30 ... ogive mold or capsule setting groove
31 ... air intake hole
32 ... water passing hole

DETAILED DESCRIPTION OF THE INVENTION

Preferably, the mold used in the present invention is provided with a temperature adjusting function in its sprue, runner and gate portions and is also provided with a mechanism for sucking and exhausting the air from the mold with ogive mold, capsule, inner plate, container or the like fitted and loaded therein.

In the process of the present invention, moreover, a particularly outstanding effect is obtained when a clamping force (F) of the mold satisfies the following expression [1]:

$$F \geq P \times S \qquad [1]$$

where,
F: mold clamping force (kg)
P: injection pressure (kg/cm$^2$)
S: projected area (cm$^2$) of a mold cavity (female mold)

The following description is now provided about a basic construction of a molding equipment used in the present invention.

The molding equipment used in the present invention basically comprises four units which are an injection unit (heating unit), a mold clamping unit (cooling unit), an oil-hydraulic unit and a control unit. The injection uinit, as shown in FIG. 1, comprises a hopper 1, an oil-hydraulic cylinder 6 for moving a screw 3 or a plunger forward to create injection pressure and speed, and a nozzle 4 positioned at the front end of the heating cylinder to inject a plasticized material into the mold. As heating methods in the heating cylinder, there are a method using a heater for direct heating and a method using a jacket for indirect heating. The latter method is preferred in view of a fine adjustment of set temperature.

As types, there are a horizontal type, a vertical type, capable of replacing molds, and a vertical type provided with several single- or plural-cavity molds on a turntable.

In the case of a cosmetic composition of low viscosity and good fluidity, the oil-hydraulic cylinder may be substituted by a water-hydraulic cylinder or an air cylinder.

On the other hand, in the case of a composition of low fluidity, for example, of high viscosity, a plunger type pushing machine may be used in place of the hopper.

The mold clamping unit comprises two platens which are fixed and movable platens for supporting the mold, and an oil-hydraulic cylinder for moving the movable platen to open and close the mold and also for generating a mold clamping force. The mold construction may be changed variously according to the shape of a desired molded product, properties of a cosmetic base used, etc. For example, there may be adopted a three-plate type mold having an additional plate between fixed and movable side molds, or a split type mold having a three or more split construction.

The oil-hydraulic unit constituted by an electric motor and a pump, which are not detailed in figures, for supply an oil pressure to the oil-hydraulic cylinders as constituents of both units described above.

The control unit has a construction for controlling the electric motor and heating device and also controlling a sequence of operations. If necessary, an automatic take-out mechanism may be incorporated therein.

Although the basic construction is as described above, there also may be adopted a construction wherein servomotors or the like are used other than oil pressure as drive sources for injection and mold clamping.

The mold is provided with a temperature adjusting mechanism using a heater or utilizing the circulation of hot water or hot oil at each of sprue, runner and gate portions and is also provided with a mechanism for exhausting the air from the mold by suction through a vent hole with ogive mold, capsule, inner plate or container (not detailed in figures) fitted and loaded into the mold.

According to the process of the present invention, various viscous cosmetics, including lipstick, foundation, eye shadow, solid powdery perfume, solid powdery deodorant and solid shaving cosmetics, can be produced by the injection of cosmetic compositions into the mold of the molding equipment described above. The solidification by cooling can be done rapidly in an extremely high efficiency, and the solid cosmetics, produced in uniform filling density and high productivity, possess a good shape retaining property, a polymorphous property which permits forming into any desired shape, a high strength, and in use, exhibit good adhesion to the skin, excellent spreading property, do not exhibit a dry or sticky impression, further, possess a superior cosmetic retaining property, not readhering to handkerchief, coffee cup or the like. Besides, in molding a cosmetic base in the molding equipment, since the cosmetic base is injected directly into the mold with ogive mold, capsule, inner plate, container or the like fitted and loaded therein, there is no fear of stain of the mold and hence the cleaning of the mold after molding is not necessary. Moreover, also at the time of taking out the resulting molded product from the mold, since the operation can be done without directly touching the cosmetic, it is possible to take out the molded product without damage thereto. Further, by setting the temperature at about the same level as that of the cosmetic base in the cylinder through the temperature adjusting mechanism provided at each of sprue, runner and gate portions, the solidification by cooling of the cosmetic base is prevented and the movement thereof into the mold can be done smoothly, thus permitting the production of a good molded product. Moreover, since the mold is provided with a mechanism for exhausting the air by suction from the mold with ogive mold, capsule, inner plate, container or the like fitted and loaded therein, the filling of the cosmetic composition into the mold can be done in a satisfactory manner without any trouble. Besides, a large number of molded products can be obtained in an instant through a single injection process, and molding conditions such as injection pressure and injection speed can be set much more widely than in the conventional injection filling method, so there is no restriction in formulation imposed on the cosmetic base used, nor is there any restriction on the shape of ogive mold, capsule, inner plate, container or the like which is fitted and loaded into the mold. Consequently, not only there can be attained a polymorphous moldability, a shape retaining property and a high strength, but also a desired sense of touch can be obtained with respect to spreading and adhesion which are important conditions required for cosmetics.

The ogive mold, capsule, inner plate, container or the like fitted and loaded into the mold may be provided with ribs, frost, beard- or tongue-like matter, or the like, whereby the adhesion between the molded cosmetic base and the ogive mold, capsule, inner plate, container or the like is improved and thus it is desirable from the standpoint of actual use.

According to the process of the present invention, as set forth above, a solid cosmetic having both a high strength and a good feeling of use can be produced by molding extremely efficiently.

The process of the present invention is applicable to any of such viscous cosmetic bases as referred to above, but when it is applied to a cosmetic base containing a solid oil and a powder base as essential ingredients, particularly such a cosmetic base using wax as at least a portion of the solid oil, there will be attained a remarkable improvement in the feeling of use such as the sense of touch of the resulting solid cosmetic. This is presumed to be because a peculiar change in condition which the cosmetic base composition undergoes during the molding operation operates effectively on fine crystallization of the wax.

The cosmetic base used in the process of the present invention contains a solid oil-containing oil and a powder base as main ingredients, with additives incorporated therein if desired. As the powder base, there may be used any of those which are usually employed in make-up cosmetics. No special limitation is placed thereon. Examples of such cosmetic powder include inorganic extender pigments such as talc, kaolin, mica, magnesium carbonate, aluminum magnesium silicate, calcium carbonate, magnesium silicate, and silica; inorganic white pigments such as titanium oxide and zinc oxide; pearling agents such as mica titanium and ion oxide-treated mica titanium; organic coloring pigments such as tarry coloring matters; organic powders such as nylon powder, polyethylene powder, acryl powder, silicon powder, Teflon powder, polyester powder, silk powder and crystal cellulose; and metallic soap powders such as zinc laurate and zinc stearate. One or more may be selected and used from among those just exemplified above. There also may be used one or more of composite powders each consisting of two or more of the cosmetic powders exemplified above.

These cosmetic powders and composite powders may have been surface-treated using a known substance such as, for example, silicone, Teflon, metallic soap, lecithin, or collagen.

As the solid oil-containing oil there may be used a liquid, semi-solid or solid oil or fat, hydrocarbon oil, ester oil, silicone oil, higher fatty acid or higher alcohol, which are usually employed in cosmetics. Examples are liquid paraffins, squalane, polybutene, paraffin wax, microcrystalline wax, ceresine wax, polyethylene, vaseline, castor oil, Jojoba oil, Macadamia nut oil, isopropyl myristate, isopropyl palmitate, isocetyl stearate, isocetyl myristate, cetyl palmitate, cetyl 2-ethylhexanoate, octyldodecyl myristate, octydodecyl trioctanoate, glyceryl trioctanoate, hydrous lanolin, dimethylpolysiloxane, methylpolysiloxane, oleic acid, and oleyl alcohol. But there is made no limitation to these examples. One or more are selected and used from among them.

As examples of additives there are mentioned antiseptic, ultraviolet ray absorber, thickening agent, inorganic salts and perfumes, provided no limitation is made thereto. Additives are used if desired.

The following apparatus- and formulation-examples are given to illustrate the present invention in more detail. It is to be understood that the invention is not limited thereto.

APPARATUS EXAMPLE 1

An example of a manufacturing process and apparatus according to the present invention will be described below with reference to the accompanying drawings.

FIG. 1 is a longitudinal sectional view of a principal portion of an apparatus showing an example which realizes molding of a solid cosmetic.

The apparatus illustrated in FIG. 1 comprises a hopper 1 into which is introduced a viscous cosmetic composition such as a composition for lipstick or foundation, a screw 3 for feeding the viscous cosmetic into a heating cylinder 2, and a nozzle 4 for injecting the cosmetic composition into a mold 5. The mold into which is injected the cosmetic composition is of a bisected construction comprising a stationary side fixed to a fixed platen and a movable side fixed to a movable platen. The apparatus is provided with a heating/cooling device (not shown) for keeping the mold heated or cooled at a predetermined certain temperature, for example, utilizing a heating or cooling action of hot or cold water.

The following description is now provided about the process of the present invention which is realized by this apparatus.

A cosmetic composition (e.g. a cosmetic base containing a solid oil-containing oil and a powder as main ingredients) for a viscous cosmetic, e.g. lipstick, is introduced from the hopper and fed to the front portion of the cylinder while being plasticized by the rotation of the screw incorporated in the heating cylinder. Then, the screw begins to retreat, and when it has retreated a preset length, the rotation of the screw stops automatically, so that a pool of the cosmetic base is formed in the front portion of the cylinder, and a predetermined amount thereof is measured.

Then, the moving-side mold begins to close and upon mold clamping at a preset pressure, the injection unit advances and the nozzle is brought into pressure contact with the fixed-side mold. Subsequently, the cosmetic base weighed in the front portion of the cylinder is injected from the nozzle tip into the mold with ogive mold, capsule, inner plate, container or the like fitted therein, at preset pressure and injection speed. At the timing just before the start of injection, the air in the mold is exhausted by suction, thereafter the cosmetic base is injected into the mold and cooled to solidify for a predetermined time while being held at the preset pressure. Then, the injection unit moves back, the mold is opened and the resulting molded product is taken out. Through these basic steps there is obtained a solid cosmetic.

APPARATUS EXAMPLE 2

An apparatus example based on an air cylinder-plunger system will now be described. FIG. 2 is a vertical sectional view of a principal portion of an apparatus according to an example of the present invention which realizes molding of a solid cosmetic. The apparatus basically comprises an air feeder 12 for feeding air to an air cylinder, the air cylinder, indicated at 13, for driving a pump shaft, a heating cylinder 14 equipped with a jacket for heat-plasticizing a cosmetic base and injecting the thus-plasticized cosmetic base into a mold, and the mold, indicated at 15, with ogive mold, capsule, inner plate, container or the like fitted therein. Basic operation steps will be described below.

A viscous cosmetic base (hereinafter referred to as "bulk") is introduced into the heating cylinder with jacket which has been heated to a preset temperature. Then, the pump shaft is brought down by the supply of air to the air cylinder to apply a constant pressure to the bulk in the heating cylinder at all times. The moving-side mold begins to close and mold clamping is performed at a preset pressure. When the gas in the mold is removed by suction by means of a degassing device (not shown), a shut-off valve disposed in the mold opens and the bulk which has been plasticized by the heating cylinder is injected at a preset pressure into the mold with ogive mold, capsule, inner plate, container or the like fitted therein. Then, in a dwelled state at the preset pressure, the shut-off valve closes, and after cooling to solidify for a predetermined time, the mold is opened and the resulting molded product is taken out. By repeating these basic steps, solid cosmetics are produced continuously. In this case, as to the type, there are horizontal and vertical types, and as to the mold mounting mode, a mold replaceable mode is preferred in point of production efficiency; for example, there may be adopted a type wherein two molds or so are used in a replaceable manner, or a type wherein plural molds are provided on a turntable.

According to the present invention, as in the above Apparatus Example 1 and/or Apparatus Example 2, the molding of a cosmetic base into a solid cosmetic can be done rapidly in an extremely high efficiency; besides, a large number of molded products can be obtained in an instant through a single process. Moreover, since a cosmetic base is injected directly into ogive mold, capsule, inner plate, container or the like, there is no fear of stain of the mold and so it is not necessary to perform cleaning of the mold after molding. Also at the time of taking out the resulting molded product from the mold, the operation can be done without directly touching the molded cosmetic, so there is no fear of damage to the product.

Thus, the molding process of the present invention for producing a solid cosmetic is extremely high in production efficiency, and the product obtained thereby is superior in the quality and characteristics, and hence the process of the present invention is of great significance in practical use.

FORMULATION EXAMPLE (1): LIPSTICK

| Composition | wt % | |
|---|---|---|
| Silicon dioxide | 5.0 | A |
| Talc | 30.0 | A |
| Mica | 25.0 | A |
| Titanium dioxide | 3.0 | A |
| Coloring matter | 2.0 | A |
| Paraffin wax | 5.0 | B |
| Diglyceryl monoisostearate | 3.0 | B |
| Neopentyl glycol dioctanoate | 7.0 | B |
| Squalane | 20.0 | |
| Total: | 100.0 | |

Figure 3:
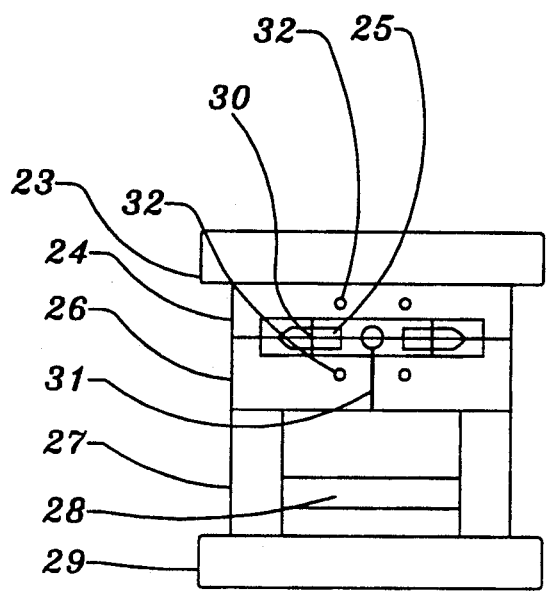
FIGS. 3 and 4 are sectional views showing an example of a mold and mold cavities for stick moldings.
Figure 4:
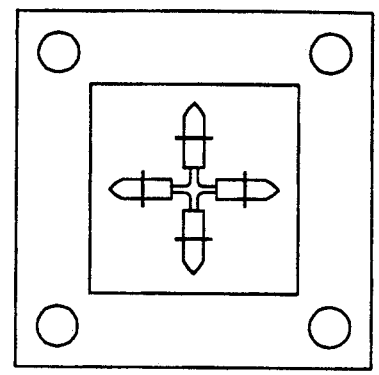

The above A and B were mixed together and, using a four-cavity mold with ogive mold and inner plate set therein, as shown in FIGS. 3 and 4, the resulting mixture was molded at a plasticization temperature of 70° C., an injection pressure of 70 kg/cm², a mold clamping force of 20 t, a mold temperature of 10° C. and an intra-mold vacuum of 50 cmHg. In a composition of 65 wt % powder and 35 wt % oil, which has heretofore been difficult to effect molding, a lipstick cosmetic was obtained as a molded product.

COMPARATIVE EXAMPLE (1): LIPSTICK

| Composition | wt % | |
|---|---|---|
| Coloing matter | 5.0 | A |
| Titanium dioxide | 3.0 | A |
| Pearl pigment | 10.0 | B |
| Paraffin wax | 5.0 | C |
| Ceresine wax | 10.0 | C |
| Candelilla wax | 2.0 | C |
| Hardened castor oil | 3.0 | C |
| Diisostearyl malate | 7.0 | C |
| Silicone oil | 8.0 | C |
| Diglyceryl triisostearate | 10.0 | C |
| Lanolin derivative | 8.0 | C |
| Liquid paraffin | 29.0 | C |
| Total: | 100.0 | |

The ingredients of the above C were melted and mixed at 80° C., then the above A was added, followed by dispersion, mixing and melting, using a roll mill, and then the above B was added and mixed therein. The resulting mixture was molded by casting, using a conventional lipstick forming mold. The product obtained was sticky and re-adhered easily to cups, etc.

COMPARATIVE EXAMPLE (2): LIPSTICK

With respect to the same composition as in Formulation Example (1), molding was tried according to a cast melting filling method, but fluidity was not obtained and it was impossible to effect molding.

FORMULATION EXAMPLE (2): EYE SHADOW

| Composition | wt % | |
|---|---|---|
| Nylon powder | 10.0 | A |
| Mica treated with metallic soap | 38.0 | A |
| Titanium dioxide | 5.0 | A |
| Pearl pigment | 15.0 | A |
| Coloring matter | 2.0 | A |
| Ceresine wax | 5.0 | B |
| Jojoba oil | 15.0 | B |
| Neopentyl glycol dicaprate | 4.0 | B |
| Glyceryl trioctanoate | 6.0 | |
| Silicone oil | 5.0 | C |
| Total: | 105.0 | |

Figure 5:
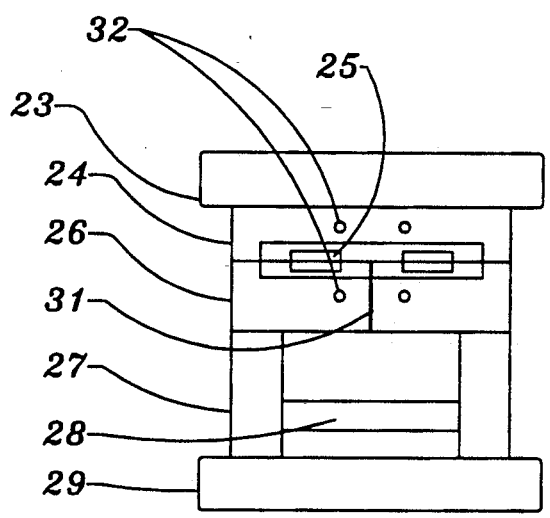
FIGS. 5 and 6 are sectional views showing an example of a mold and mold cavities for flat moldings.
Figure 6:
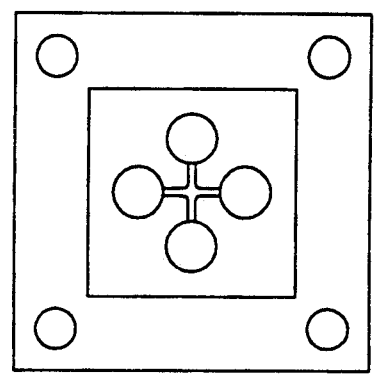

The ingredients of the above B were melted and mixed together, then the above C was added and the temperature was adjusted to 50° C., followed by mixing with the above A. The resulting mixture was molded using a mold with capsules set therein, as shown in FIGS. 5 and 6, at a plasticization temperature of 50° C., an injection pressure of 50 kg/cm², a mold clamping force of 10 t, a mold temperature of 20° C. and a vacuum of 40 cmHg. The molded products were dried at 80° C. to remove the silicone oil. Both moldability and the sense of touch were satisfactory.

COMPARATIVE EXAMPLE (3): EYE SHADOW

| Composition | wt % | |
|---|---|---|
| Silicon dioxide | 5.0 | A |
| Mica | 10.0 | A |
| Talc | 57.0 | A |
| Kaolin | 5.0 | A |
| Titanium dioxide | 5.0 | A |
| Coloring matter | 5.0 | B |
| Paraffin wax | 2.0 | B |
| Neopentyl glycol dicaprate | 3.0 | B |
| Isostearyl myristate | 3.0 | B |
| Squalane | 5.0 | |
| Total: | 100.0 | |

The ingredients of the above B were melted and mixed together using a Henschel mixer and the resulting mixture was mixed with the above A under stirring, followed by pulverization using a hammer mill and subsequent press molding.

FORMULATION EXAMPLE (3): FOUNDATION

| Composition | wt % | |
|---|---|---|
| Silicon dioxide | 5.0 | |
| Talc | 28.0 | |
| Mica | 25.0 | |
| Titanium dioxide | 5.0 | |
| Coloring matter | 2.0 | |
| Microcrystalline wax | 4.0 | |
| Paraffin wax | 2.0 | |
| Diglyceryl diisostearate | 7.0 | |
| Diisostearyl malate | 2.0 | |
| Jojoba oil | 20.0 | |
| Total: | 100.0 | |

The above A and B were mixed together and then molded using a mold with inner plates set therein, the inner plates each having an inlet, as shown in FIGS. 5 and 6, at a plasticization temperature of 70° C., an injection pressure of 150 kg/cm, a mold clamping force of 30 t, a mold temperature of 10° C. and an intra-mold vacuum of 50 cmHg. As a result, there was obtained a foundation as an intermediate molded product between a viscous press type heretofore difficult to effect molding and a liquid cast type. The sense of touch was very good as noted previously

COMPARATIVE EXAMPLE (4): FOUNDATION

| Composition | wt % |
|---|---|
| Silicon dioxide | 5.0 |

-continued

| Composition | wt % | |
|---|---|---|
| Mica | 25.0 | A |
| Talc | 50.0 | A |
| Titanium dioxide | 5.0 | A |
| Kaolin | 3.0 | A |
| Coloring matter | 2.0 | |
| Paraffin wax | 1.0 | B |
| Neopentyl glycol dicaprate | 2.0 | B |
| Liquid paraffin | 7.0 | B |
| Total: | 100.0 | |

The ingredients of the above B were melted and mixed together using a Henschel mixer and the resulting mixture was further mixed with the above A under stirring, followed by pulverization using a hammer mill. This cosmetic composition was mixed with an organic solvent at a mixing ratio of 1:2 in terms of weight percent and the resulting mixture was filled and molded in a metal plate according to the method described in Japanese Patent Laid Open No. 127305/1981.

COMPARATIVE EXAMPLE (5): FOUNDATION

The composition described in Formulation Example (3) was molded using the mold shown in FIGS. 5 and 6 with inner plates set therein, the inner plates each having an inlet, at a plasticization temperature of 70° C., an injection pressure of 150 kg/cm$^2$, a mold clamping force of 30 t, a mold temperature of 10° C. and an intra-mold vacuum of 0 cmHg. In the case where the air in the mold was not exhausted by suction, the resulting molded products were unsatisfactory, with air bubbles remaining in the interior of each molded product and weldline formed thereon.

FORMULATION EXAMPLE (4): FOUNDATION

The composition described in Formulation Example (3) was molded using the four-cavity mold (mold cavity projected area: S=120 cm$^2$) shown in FIGS. 5 and 6 with inner plates set therein, the inner plates each having an inlet, at a plasticization temperature of 70° C., an injection pressure of P=70 kg/cm$^2$ and hence a mold clamping force of $F_0 = P \times S = 8,400$ kg/cm$^2$, a mold clamping force of $F_1 = 9,000$ kg/cm$^2$, a mold temperature of 10° C. and an intra-mold vacuum of 40 cmHg. When the molding clamping force was $F_1$, larger than $F_0$, both the mold and the molded products obtained were clean.

COMPARATIVE EXAMPLE (6): FOUNDATION

The composition described in Formulation Example (3) was molded using the four-cavity mold (mold cavity projected area: S=120 cm$^2$) shown in FIGS. 5 and 6 with inner plates set therein, the inner plates each having an inlet, at a plasticization temperature of 70° C., an injection pressure of P=70 kg/cm$^2$ and hence a mold clamping force of $F_0 = P \times S = 8,400$ kg, a mold clamping force of $F_2 = 4,000$ kg, a mold temperature of 10° C. and an intra-mold vacuum of 40 cmHg. When the mold clamping force was $F_2$, smaller than $F_0$, the composition protruded from the mold cavities because of deficiency of the mold clamping force, resulting in that the mold was stained and the molded products obtained were burred and thus unsatisfactory.

TABLE 1

| Kind | Lipstick | | | Eye Shadow | | Foundation | |
|---|---|---|---|---|---|---|---|
| Sample | Ex. 1 | Com. Ex. 1 | Com. Ex. 2 | Ex. 2 | Com. Ex. 3 | Ex. 3 | Com. Ex. 4 |
| Shape | shell-shaped | shell-shaped | shell-shaped | flat | flat | flat | flat |
| Polymorphous Property | good | moderate | moderate | good | bad | good | moderate |
| Breaking Strength (g) | 500 | 250 | 250 | — | — | — | — |
| Drop Strength (number of times) | — | — | — | >10 | 3 | >10 | 2 |
| Productivity | good | moderate | good | good | moderate | good | bad |
| Re-adhesion to Handkerchief and Cup | not adhered | adhered | adhered | not adhered | slightly adhered | not adhered | slightly adhered |
| Feeling of Use | good | sticky | sticky | good | dry | good | dry |

Breaking Strength: Using a rheometer NRM-2002J, a molded product is fixed, then in a position spaced 10 mm from that position, a load is applied at a rate of 2 mm/sec until the molded product is broken, and the value of the breakage load is used as the breaking strength.

Diameter of Molded Product: 9 mm

Drop Strength: A molded product is gravity-dropped from a height of 50 cm onto a 20 mm thick plywood, and the number of times of the dropping until initial cracking or fissure of the molded product is used as the drop strength.

Metal Plate: 58 mm in diameter, 5 mm in height

As is apparent also from Table 1 which makes comparison between working examples of the present invention and comparative examples, the process of the present invention is superior in both productivity and polymorphous property, and the cosmetics obtained by the process of the invention have a satisfactory shape retaining property and a sufficient strength (partiicularly, the stick cosmetics obtained by the process of the invention are superior in the adhesion to the skin and puff and have a breaking strength twice as high as the conventional products, the relation between such adhesion and breaking strength being the most important point). In practical use, moreover, the cosmetics produced according to the process of the present invention were soft to the touch, superior in their cosmetic retaining property and did not re-adhere to handkerchief and coffee cup, thus having excellent characteristics.

What is claimed is:

1. A process of producing a solid cosmetic by molding, comprising continuously repeating the steps of feeding a cosmetic base containing a powder and an oil as main ingredients into a heating cylinder from a hopper, said heating cylinder incorporating a screw or a plunger therein, causing said cosmetic base to be heated and then injected into a clamped single- or plural-cavity mold by a forward movement of the screw or the plunger, and cooling the thus-injected cosmetic base to solidify in the mold.

2. A process according to claim 1, wherein said mold is provided at sprue, runner and gate portions with a temperature adjusting function and/or a function of exhausting air by suction from the mold.

3. A process according to claim 1, wherein an ogive mold, capsule, inner plate, or container can be fitted and loaded into said mold.

4. A process according to claim 1, wherein a clamping force of said mold is represented by the following expression [1]:

$$F \geq P \times S \qquad [1]$$

where,
F: clamping force (kg);
P: injection pressure (kg/cm$^2$);
S: projected area (cm$^2$) of mold cavity (female mold).

* * * * *